(12) United States Patent
Jiang et al.

(10) Patent No.: US 10,702,187 B2
(45) Date of Patent: Jul. 7, 2020

(54) APPARATUS AND METHOD FOR CONTROLLING RADIATION SOURCE VARIABILITY FOR OPTICAL GAS MEASUREMENT SYSTEMS

(75) Inventors: Zhi-Xing Jiang, Southbury, CT (US); Anthony Pierry, Plantsville, CT (US)

(73) Assignee: Koninklijke Philips N.V., Eindhoven (NL)

( * ) Notice: Subject to any disclaimer, the term of this patent is extended or adjusted under 35 U.S.C. 154(b) by 350 days.

(21) Appl. No.: 14/113,528

(22) PCT Filed: Apr. 4, 2012

(86) PCT No.: PCT/IB2012/051647
§ 371 (c)(1),
(2), (4) Date: Oct. 23, 2013

(87) PCT Pub. No.: WO2012/153209
PCT Pub. Date: Nov. 15, 2012

(65) Prior Publication Data
US 2014/0052003 A1 Feb. 20, 2014

Related U.S. Application Data

(60) Provisional application No. 61/479,132, filed on Apr. 26, 2011.

(51) Int. Cl.
*A61B 5/00* (2006.01)
*A61B 5/08* (2006.01)
(Continued)

(52) U.S. Cl.
CPC .............. *A61B 5/082* (2013.01); *G01J 3/108* (2013.01); *G01N 21/274* (2013.01); *G01N 21/3504* (2013.01); *G01N 21/85* (2013.01)

(58) Field of Classification Search
CPC combination set(s) only.
See application file for complete search history.

(56) References Cited

U.S. PATENT DOCUMENTS 5,159,934 A * 11/1992 Hoberman ........... A61B 5/0836
422/84
5,369,278 A 11/1994 Lehto
(Continued)

FOREIGN PATENT DOCUMENTS

| DE | 102009011421 B3 | 4/2010 |
|---|---|---|
| EP | 1720001 A1 | 11/2006 |
| WO | 199922400 A1 | 5/1999 |

OTHER PUBLICATIONS

Huang et al., "Effects of performance parameters of feedback components on thermoelectric gas sensors", Journal of Functional Materials and Devices (Oct. 31, 2008), vol. 5, No. 883-888.

*Primary Examiner* — Joseph M Santos Rodriguez
(74) *Attorney, Agent, or Firm* — Daniel H. Brean (57) ABSTRACT

An infrared detector includes a radiation source configured to emit electromagnetic radiation. The detector includes a source monitoring apparatus configured to generate output signals (62) related to electrical resistance through the radiation source. The output signals are used to account for radiation source temperature in measurements by the detector. The output signals may be used (72) in the provision of power to the radiation source to maintain the temperature of the detector at a beneficial level. The detector is configured to monitor a level of a gaseous molecular species within a flow of breathable gas.

15 Claims, 4 Drawing Sheets

(51) Int. Cl.
    *G01N 21/3504*    (2014.01)
    *G01J 3/10*    (2006.01)
    *G01N 21/27*    (2006.01)
    *G01N 21/85*    (2006.01)

(56) References Cited

U.S. PATENT DOCUMENTS

| | | | |
|---|---|---|---|
| 6,325,978 B1 * | 12/2001 | Labuda | A61B 5/0833 |
| | | | 422/84 |
| 7,063,667 B1 * | 6/2006 | Ben-Oren | A61B 5/0836 |
| | | | 422/84 |
| 7,332,719 B2 * | 2/2008 | Frodl | G01J 3/10 |
| | | | 250/343 |
| 8,233,150 B2 | 7/2012 | Kesteren | |
| 2003/0216660 A1 * | 11/2003 | Ben-Oren | A61B 5/083 |
| | | | 600/532 |
| 2005/0018184 A1 * | 1/2005 | Imura | G01J 3/10 |
| | | | 356/300 |
| 2005/0151082 A1 * | 7/2005 | Coffin et al. | 250/339.06 |
| 2005/0259254 A1 * | 11/2005 | Soller | G01J 3/08 |
| | | | 356/328 |
| 2005/0285055 A1 * | 12/2005 | DelFavero | G01N 21/3504 |
| | | | 250/504 R |
| 2006/0249681 A1 * | 11/2006 | Frodl | 250/343 |
| 2007/0167683 A1 * | 7/2007 | Couvillon, Jr. | A61B 1/00055 |
| | | | 600/118 |
| 2008/0116378 A1 * | 5/2008 | Frodl | G01N 21/3504 |
| | | | 250/338.5 |
| 2009/0124918 A1 | 5/2009 | Stockmann et al. | |
| 2012/0161021 A1 * | 6/2012 | Smargiassi | G01N 21/33 |
| | | | 250/372 |
| 2014/0052003 A1 | 2/2014 | Jiang et al. | |

* cited by examiner

APPARATUS AND METHOD FOR CONTROLLING RADIATION SOURCE VARIABILITY FOR OPTICAL GAS MEASUREMENT SYSTEMS

CROSS-REFERENCE TO PRIOR APPLICATIONS

This application is the U.S. National Phase application under 35 U.S.C. § 371 of International application No. PCT/IB2012/051647, filed on Apr. 4, 2012, which claims the benefit of U.S. Provisional Patent Application No. 61/479,132, filed on Apr. 26, 2011. These applications are hereby incorporated by reference herein.

BACKGROUND

1. Field

The present disclosure pertains to a method and apparatus for improved gas measurement by infrared spectroscopy through compensating and/or regulating the infrared source.

2. Description of the Related Art

Systems that perform the measurement of gas levels based on the measurement of infrared electromagnetic radiation that has passed through the gas are known. In such systems, the emission parameters of a radiation source may change as the temperature of the radiation source migrates (e.g., within a single use session, over several sessions, etc.). These changes in emission parameters may increase warm-up time requirements, reduce accuracy, require field calibrations, and/or be associated with other drawbacks.

SUMMARY

Accordingly, one or more aspects of the present disclosure relate to a detector configured to monitor a level of a gaseous molecular species within a flow of breathable gas. In one embodiment, the detector comprises a source, source optics, a radiation sensor assembly, a source monitoring apparatus, and a processor. The source is configured to emit electromagnetic radiation. The source optics are configured to direct electromagnetic radiation emitted by the source across a flow path of a flow of breathable gas that communicates with an airway of a subject. The radiation sensor assembly is configured to receive electromagnetic radiation that has been emitted by the source and has passed through the flow path. The sensor assembly is further configured to generate output signals that convey information related to a parameter of the received electromagnetic radiation. The source monitoring apparatus is configured to generate output signals that convey information related to electrical resistance through the source. The processor is configured to determine a level of a gaseous molecular species within the flow of breathable gas in the flow path based on the output signals generated by the radiation sensor assembly. The processor is further configured such that the determination of the level of the gaseous molecular species is further based on the output signals generated by the source monitoring apparatus to account for the electrical resistance through the source.

Yet another aspect of the present disclosure relates to a method of monitoring a level of a gaseous molecular species within a flow of breathable gas. In some embodiments, the method comprises directing electromagnetic radiation emitted by a radiation source across a flow path of a flow of breathable gas that communicates with an airway of a subject; receiving electromagnetic radiation that has been emitted and has passed through the flow path; generating output signals that convey information related to a parameter of the received electromagnetic radiation; generating output signals that convey information related to electrical resistance through the source; and determining a level of a gaseous molecular species within the flow of breathable gas in the flow path based on the output signals conveying information related to the parameter of the received electromagnetic radiation, wherein the determination is further based on the output signals conveying information related to the electrical resistance through source.

Still another aspect of present disclosure relates to a system for monitoring a level of a gaseous molecular species within a flow of breathable gas. In some embodiments, the system comprises means for directing electromagnetic radiation emitted by a radiation source across a flow path of a flow of breathable gas that communicates with an airway of a subject; means for receiving electromagnetic radiation that has been emitted and has passed through the flow path; means for generating output signals that convey information related to a parameter of the received electromagnetic radiation; means for generating output signals that convey information related to electrical resistance through the source; and means for determining a level of a gaseous molecular species within the flow of breathable gas in the flow path based on the output signals conveying information related to the parameter of the received electromagnetic radiation, wherein the determination is further based on the output signals conveying information related to the electrical resistance through source to account for the electrical resistance through the source.

These and other objects, features, and characteristics of the present displosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
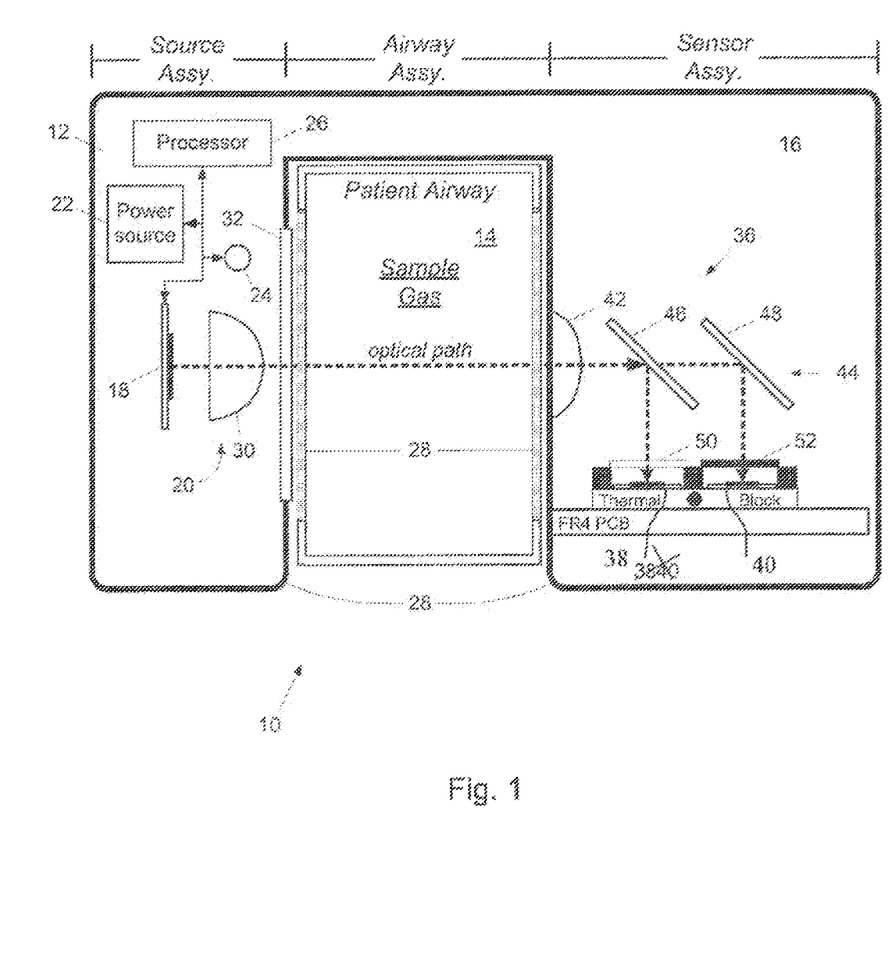
FIG. 1 is a system configured to measure a level of a molecular gaseous species in a flow of breathable gas.

FIG. 1 illustrates a detector 10 configured to measure a level of a gaseous molecular species in a flow of breathable gas. The gaseous molecular species may be carbon dioxide and/or other gaseous molecular species. For convenience, particular reference is made below to measurement of carbon dioxide. It will be appreciated that such references are not limiting, and that the principles described with respect to the measurement of carbon dioxide could be practiced in the measurement of other gaseous molecular species without departing from the scope of this disclosure. Further, description herein of detector 10 being configured to measure the level of a gaseous molecular species in a respiratory therapy context is not limiting. The principles described herein are equally applicable to other systems that perform gas level measurement in other contexts (e.g., air quality detectors, automobile emissions detectors, and/or other systems).

In one embodiment, detector 10 includes a "U" shaped housing 28 enclosing a source assembly 12, a hollow airway assembly 14, a radiation sensor assembly 16, and/or other components. Two opposing legs of the "U" shaped housing 28 define opposite sides of a gap therebetween, with the source assembly 12 disposed in one leg on one side of the gap (source side) and the radiation sensor assembly 16 disposed in the opposing leg on the opposite side of the gap (detector side). The detector 10 also includes self-contained electronics (some of which are shown in FIG. 1 and described below) disposed within the housing 28.

The airway assembly 14 forms a flow path for a flow of breathable gas that communicates with the airway of a subject. The airway assembly 14 has windows 28 disposed on opposite sides such that infrared radiation entering the flow path via the window 28 on one side of the airway assembly 14 passes through the flow of breathable gas (patient respiration) in the airway assembly 14 and exits via the window 28 on the opposite side. The airway assembly 14 may be either a disposable unit or a reusable unit that removably clips into the gap in the "U" shaped housing, with the source assembly 12 and radiation sensor assembly 16 being generally arranged such that infrared radiation emanating from the source assembly is directed across the gap through the gas sample in the airway assembly 14 to impinge upon the radiation sensor assembly 16. The airway windows 28 may be formed of plastic film (disposable version), sapphire (reusable version) and/or other materials.

The source assembly 12 includes a radiation source 18, optics 20, a power source 22, a source monitoring apparatus 24, a processor 26, and/or other components. Radiation source 18 produces broadband radiation including an "MWIR" (Mid-Wavelength InfraRed) band Infrared radiation generally refers to radiation occupying a band of wavelengths in the optical spectrum between 0.7 μm and 300 μm. "MWIR" generally refers to a mid-wavelength subset of the infrared radiation band between 3 μm and 8 μm. MWIR radiation emitted by the radiation source 18 includes a reference wavelength and a carbon dioxide wavelength ($\lambda_{REF}$ and $\lambda_{CO2}$, respectively). The radiation source 18 may operate substantially as a blackbody for at least a portion of the spectrum (e.g., between 0.7 μm and 300 μm).

The optics 20 are configured to direct electromagnetic radiation emitted by radiation source 18 across the flow path formed by airway assembly 14. The optics 20 may include a lens 30, a window 32, and/or other components. The lens 30 may be a sapphire half-ball lens that gathers and collimates the emitted radiation, directing it across the gap and through the airway assembly 14 towards the radiation sensor assembly 16 via the window 32.

The power source 22 may be configured to provide power to radiation source 18. The power source 22 may include, for example, a battery, a capacitor, a power converter, a port or connector configured to receive power from an external source (e.g., a wall socket, a monitor, and/or other external power sources), and/or other sources of power. The power source 22 is configured to deliver power in a pulsed manner, in order to cause the radiation emitted by radiation source 18 to be pulsed. To accomplish this, power source 22 may vary the potential, current, power, and/or other parameters of the electrical power provided to radiation source 18. In one embodiment, the power is provided to radiation source 18 such that radiation source 18 is pulsed at about 100 Hz to produce a periodically varying MWIR signal with a period of about 10 milliseconds.

The source monitoring apparatus 24 is configured to generate output signals conveying information related to one or more parameters of power through radiation source 18. Such parameters may include, for example, current, potential, power, resistance, induction, and/or other parameters. In some embodiments, the resistance through radiation source 18 is of particular interest. As such, the one or more parameters may include resistance itself, and/or other parameters from which resistance through radiation source 18 can be determined. The source monitoring apparatus 24 may be integrated with power source 22 and/or radiation source 18, or may be formed separately as illustrated in FIG. 1.

The processor 26 is configured to provide information processing capabilities in detector 10. As such, processor 26 may, include one or more of a digital processor, an analog processor, a digital circuit designed to process information, an analog circuit designed to process information, a state machine, and/or other mechanisms for electronically processing information. Although processor 26 is shown in FIG. 1 as a single entity, this is for illustrative purposes only in some implementations, processor 26 may include a plurality of processing units. These processing units may be physically located within the same device, or processor 26 may represent processing functionality of a plurality of devices operating in coordination. The operation of processor 26 is discussed further below. The illustration of processor 26 as being included within detector 10 is not intended to be limiting. Some or all of the functionality attributed herein to processor 26 may be provided by one or more components disposed outside of detector 10.

The radiation sensor assembly 16 includes optics 36, a first sensor 38, a second sensor 40, and/or other components. The optics 36 are configured to direct the electromagnetic radiation that has passed through the flow path formed by airway assembly onto first sensor 38 and second sensor 40. In some embodiments, the optics 36 comprise a lens assembly 42, a beam splitter assembly 44, and/or other optical components. The lens assembly 42, which in one embodiment includes an AR-coated (Anti-Reflective coated) silicon plano-convex lens, focuses the MWIR radiation reaching it from the source assembly 12, and directs the electromagnetic radiation toward first sensor 38 and second sensor 40 via beam splitter assembly 44. In beam splitter assembly 44, a dichroic beam-splitter 46 is positioned to reflect IR radiation containing the carbon dioxide wavelength $\lambda_{CO2}$ towards first sensor 38, and to pass IR radiation containing the reference wavelength $\lambda_{REF}$ towards second sensor 40 via a turning mirror 48. A narrow-band first optical filter 50 that passes $\lambda_{CO2}$ is positioned in front of first sensor 38. A narrow-band second optical filter 52 that passes $\lambda_{REF}$ is positioned in front of second sensor 40.

The basic principle of operation behind Capnometry/Capnography via detector 10 is that infrared radiation in a band around 4.275 μm experiences increasing absorption (when traveling a fixed-length path through a sample gas) with increasing carbon dioxide concentration—according to a reliably repeatable relationship. By way of comparison, the absorption of 3.681 μm infrared radiation under the same conditions is essentially unaffected by carbon dioxide concentration.

When the MWIR radiation from radiation source 18 passes through the body of gas in airway assembly 14, IR radiation at $\lambda_{CO2}$ is attenuated according to the concentration of carbon dioxide in the body of gas. IR radiation at $\lambda_{REF}$, however, is unaffected by any carbon dioxide in the body of gas, and varies only with the intensity of the IR radiation from radiation source 18. Since $\lambda_{REF}$ and $\lambda_{CO2}$ are fairly close together on the black-body radiation curve, the output signals of first sensor 38 and second sensor 40, which are sensitive to IR electromagnetic radiation, will be approximately proportional to one another over small variations in source radiation intensity as long as carbon dioxide concentration in the body of gas remains constant. By "zeroing" detector 10 with $N_2$ (or with room air—after making appropriate compensation for residual carbon dioxide in the atmosphere), a reference ratio between the output signal levels from first sensor 38 and second sensor 40 is established. Whenever the ratio between the two signals is equal to this reference ratio, there is no carbon dioxide in airway assembly 14. Any decrease in the output signal of the first sensor 38 relative to output signal of second sensor 40 indicates a corresponding increase in the concentration of carbon dioxide in airway assembly 14.

The electromagnetic radiation emitted by radiation source 18 may change with ambient temperature changes, particularly during equipment warm-up intervals which often last from two minutes to as long as two hours. Such changes in ambient temperature may be caused by heat emitted by radiation source 18 itself. The changes in the electromagnetic radiation may include intensity changes, spectral shift, and/or other changes. In some applications such as respiratory monitoring performed by detector 10 in FIG. 1, excessive warm-up times are unacceptable, and in many clinical settings a nearly instantaneous measurement is desirable. In addition, changes in output of radiation source 18 will cause errors if not compensated for.

In conventional systems, a field calibration (or zeroing) may be needed periodically to correct for such sources of measurement drift. Alternatively, automatic zeroing is sometimes employed, whereby a sample of reference gas (typically room air or some other reference) is periodically inserted into the optical path between source assembly 12 and sensor assembly 16 and used to re-establish a zero point. Such zeroing systems are costly and have an additional drawback in that the measurement must be interrupted regularly to perform the zeroing. In many applications, such as in respiratory gas monitoring, such interruptions are undesirable.

The processor 26 is configured to receive the output signals generated by sensor assembly 16 (e.g., generated by first sensor 38 and second sensor 40), and to determine from the output signals the level of carbon dioxide in the flow path formed by airway assembly 14 (e.g., in accordance with the principles described herein). Determining the level of carbon dioxide may include determining a concentration of carbon dioxide, determining an amount of carbon dioxide, determining a partial pressure of carbon dioxide, determining a mole fraction of carbon dioxide, and/or determining other levels of carbon dioxide. The processor 26 is further configured such that the determination of the level of carbon dioxide accounts for the operating temperature of radiation source 18. To account for the operating temperature of radiation source 18, processor 26 is configured to adjust the determination of the level of carbon dioxide based on the output signals generated by source monitoring apparatus 24.

Figure 2:
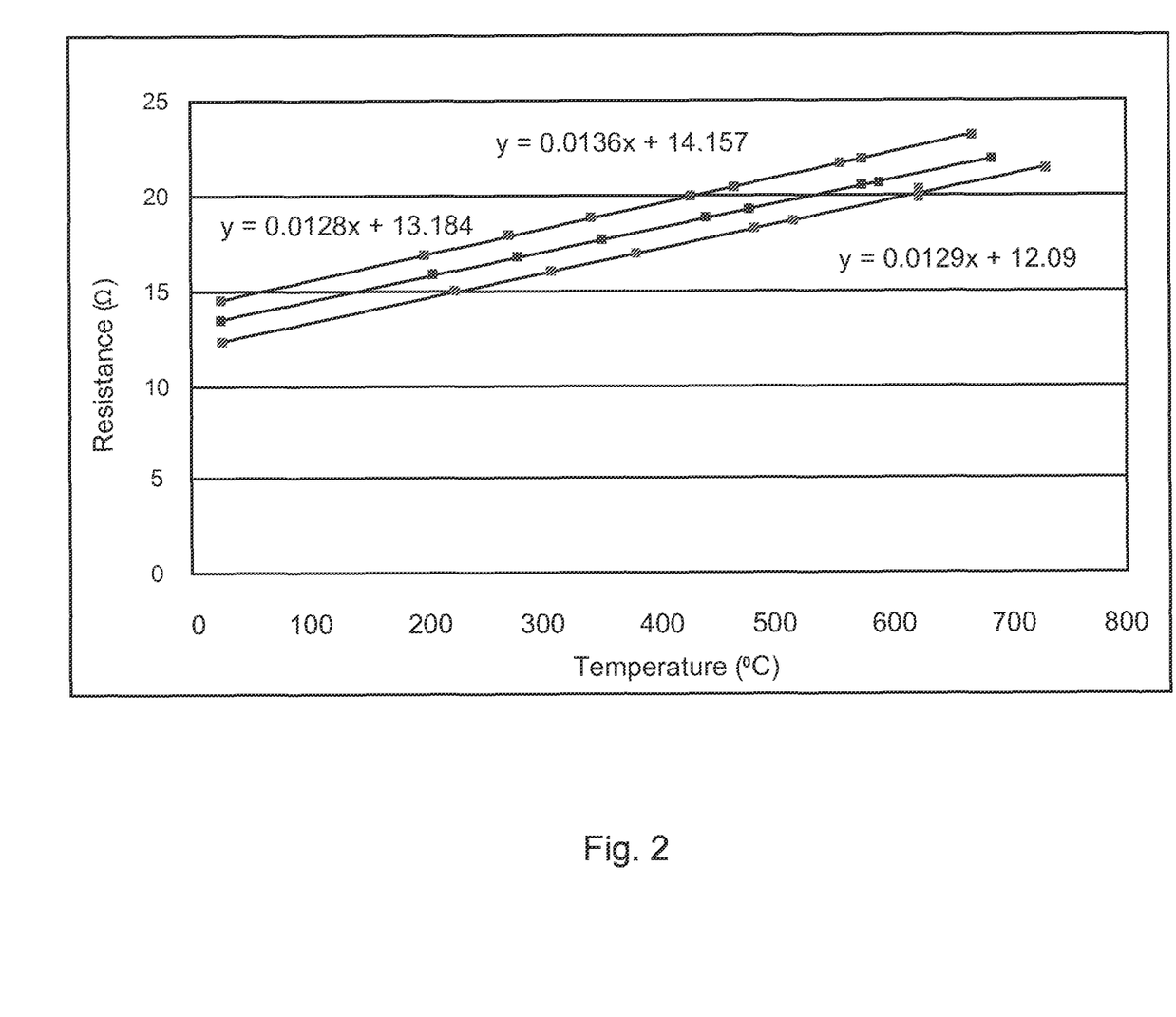
FIG. 2 is a plot showing correlations between electrical resistance and temperature and a plurality of radiation sources.

The electrical resistance through radiation source 18 correlates with the temperature of radiation source 18. This correlation may be determined in advance, and may be available to, or included in the logic of, processor 26. By way of illustration, FIG. 2 illustrates the correlation between electrical resistance and temperature in several sources that are similar to or the same as radiation source 18 (shown in FIG. 1 and described herein). As can be seen in FIG. 2, the correlation may be approximated for use by a processor as a polynomial function, as a straight line function, and/or as other functions that describe temperature as a function of electrical resistance.

Referring back to FIG. 1, processor 26 is configured to implement the predetermined correlation between electrical resistance and temperature within radiation source 18 to adjust determinations of the level of carbon dioxide. Adjustments are determined based on the output signals generated by source monitoring apparatus 24, because the output signals generated by source monitoring apparatus 24 convey information related to electrical resistance through source monitoring apparatus 24. Adjusting determinations of the level of carbon dioxide based on the output signals generated by source monitoring apparatus 24 may reduce or eliminate issues present in conventional detectors as a result of temperature drift in the radiation source. For example, this may reduce inaccuracy caused by temperature fluctuations, and/or may eliminate the need for field calibrations.

Figure 3:
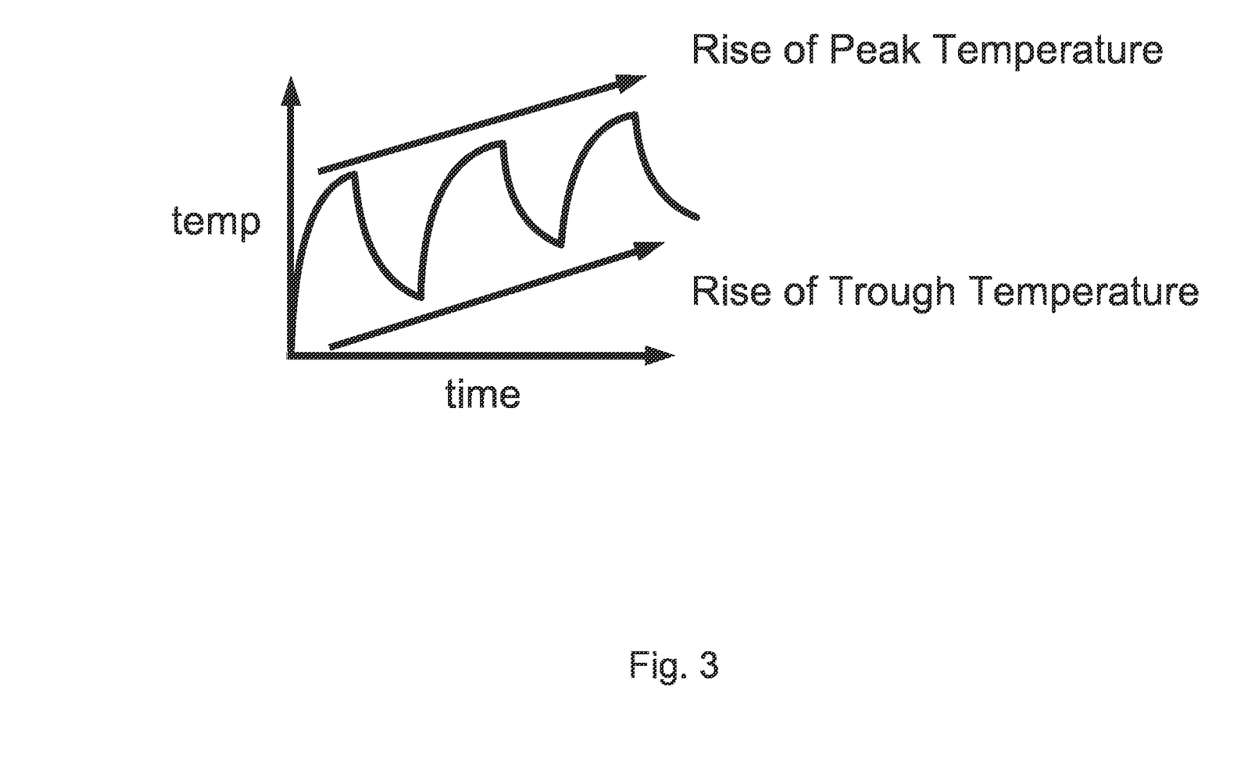
FIG. 3 is a plot showing temperature over time in a radiation source used to emit pulses of electromagnetic radiation.

As was mentioned above, during operation, radiation source 18 is pulsed to provide a pulsed stream of electromagnetic radiation. The pulsing of radiation source 18 causes the temperature of radiation source 18 to fluctuate. By way of non-limiting illustration, FIG. 3 depicts a plot showing temperature versus time for a radiation source that is being pulsed. As can be seen in FIG. 3, over time as the temperature of the radiation source oscillates with the pulses, the temperature trends generally higher. For example, as is shown, the peak temperatures and/or the trough temperatures over time trend higher.

Referring back to FIG. 1, in some embodiments, in correcting for the temperature of radiation source 18, processor 26 is configured to determine the temperature of radiation source 18 as a value that does not oscillate on a pulse-by-pulse basis. For example, temperature may be considered to be the temperature at a given phase of the pulse oscillations (e.g., the peak temperature, the trough temperature, the median temperature, and/or other phases). As another non-limiting example, the temperature may be an average value taken over some sliding window in time.

In some embodiments, processor 26 implements the indication of source temperature provided by the output signals of source monitoring apparatus 24 for purposes other than adjustment of the determination of the level of carbon dioxide. For example, processor 26 may be configured to control the provision of power to radiation source 18 from power source 22. The provision of power radiation source 18 can be regulated based on the indication of source temperature provided by the output signals of source monitoring apparatus 24. Such regulation may include reducing and/or increasing power levels to account for changes in intensity caused by temperature migration. Regulating the power provided to radiation source 18 may include adjusting the level(s) of power provided to radiation source 18 (e.g., a pulse energy, a peak power, a trough power, and/or other power levels), the timing of pulses (e.g., period, frequency, pulse-length, and/or other timing parameters) to maintain the temperature (e.g., the peak temperature) of radiation source 18 within a range, below a threshold, and/or within other bounds.

Temperature management of radiation source 18 by processor 26 may enhance the operation of detector 10 in a variety of ways. For instance, the power efficiency of radiation source 18 may increase with temperature. However, various design parameters may make very high temperatures undesirable. For example, excessive operating temperatures may reduce the life of radiation source 18 through wear-out or burn-out. By maintaining the temperature of radiation source 18 within certain constraints, efficiency may be enhanced without inducing temperatures in radiation source 18 which may significantly reduce the life of radiation source 18.

In some embodiments, processor 26 is configured to estimate irradiance of radiation source 18 based on the output signals generated by source monitoring apparatus. For example, processor 26 may estimate irradiance as a function of resistance through radiation source 18, potential across radiation source 18, current through radiation source 18, and/or other parameters. The processor 26 may be connected with first sensor 38 and/or second sensor 40 to receive the output signals generated by sensors 38 and/or 40. In particular, the output signals generated by second sensor 40, which pertain to one or more parameters of received electromagnetic radiation in $\lambda_{REF}$, can be used by processor 26 to determine measured irradiance. By comparing the estimated irradiance with the measured irradiance, processor 26 can monitor one or more system parameters that could potentially impact gas measurement accuracy. For example, relatively large differences in estimated and measured irradiance may indicate a change along the optical path from radiation source 18 to first sensor 38 and/or second sensor 40. Responsive to determination that the difference between the measured irradiance and the estimated irradiance breach a threshold, processor 26 may generate a notification or alarm for a user (e.g., the subject, a caregiver, an equipment maintenance person, and/or other users), initiate a recalibration of detector 10, and/or take other actions.

In some embodiments, the estimated irradiance determined by processor 26 is used to calculate the level of carbon dioxide, instead of actually measuring irradiance at a reference wavelength. This may reduce the cost of parts and/or assembly, reduce complexity of the system, and/or provide other benefits. For example, since a measurement in $\lambda_{REF}$ is no longer needed to provide a measurement of irradiance, second sensor 40 may be eliminated from the design. The estimated irradiance is then used in place of the signal generated by second sensor 40.

Figure 4:
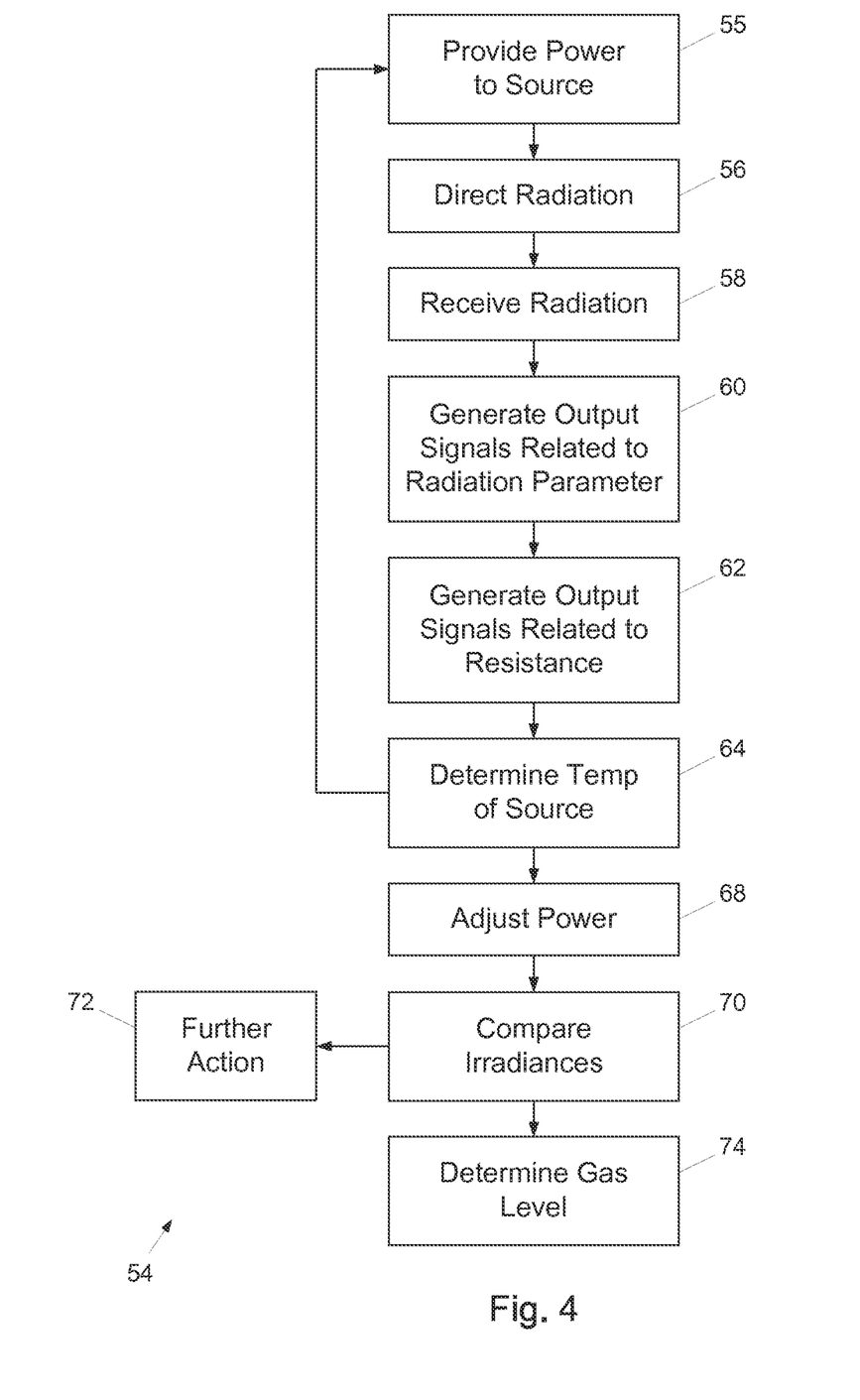
FIG. 4 illustrates a method of measuring a level of a molecular gaseous species in a flow of breathable gas.

FIG. 4 illustrates a method 54 of monitoring a level of a gaseous molecular species within a flow of breathable gas. The operations of method 54 presented below are intended to be illustrative. In some embodiments, method 54 may be accomplished with one or more additional operations not described, and/or without one or more of the operations discussed. Additionally, the order in which the operations of method 54 are illustrated in FIG. 4 and described below is not intended to be limiting.

In some embodiments, method 54 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 54 in response to instructions stored electronically on an electronic storage medium. The one or more processing devices may include one or more devices configured through hardware, firmware, and/or software to be specifically designed for execution of one or more of the operations of method 54.

At an operation 55, power is provided to a radiation source that causes the radiation source to emit electromagnetic radiation. The power may be provided to the radiation source such that the electromagnetic radiation is emitted in a pulsed manner. In one embodiment, the radiation source is similar to or the same as radiation source 18 (shown in FIG. 1 and described herein). In one embodiment, operation 55 is performed by a power source similar to or the same as power source 22 (shown in FIG. 1 and described herein).

At an operation 56, electromagnetic radiation emitted by the radiation source is directed across a flow path of a flow of breathable gas that communicates with an airway of a subject. In one embodiment, the flow path is formed by an airway assembly similar to or the same as airway assembly 14 (shown in FIG. 1 and described herein). Operation 56 may be performed by a set of optics similar to or the same as optics 20 (shown in FIG. 1 and described herein).

At an operation 58, electromagnetic radiation emitted at operation 56 that has passed through the flow path is received. In one embodiment, operation 58 is performed by a sensor assembly similar to or the same as sensor assembly 16 (shown in FIG. 1 and described herein).

At an operation 60, output signals that convey information related to a parameter of the received electromagnetic radiation are generated. The parameter may include intensity, wavelength, phase, and/or other parameters. In one embodiment, operation 60 is performed by one or more sensors similar to or the same as first sensor 38 and/or second sensor 40 (shown in FIG. 1 and described herein).

At an operation 62, output signals that convey information related to electrical resistance through the source are generated. For example, the output signals may indicate potential across the source, current through the source, and/or other parameters of electrical energy through the source. In one embodiment, operation 62 is performed by a source monitoring apparatus similar to or the same as source monitoring apparatus 24 (shown in FIG. 1 and described herein).

At an operation 64, a temperature of the radiation source is determined based on the output signals generated at operation 62. If the radiation source is being pulsed, the temperature determined may be the temperature at a given phase in the pulse oscillations (e.g., a peak temperature, a trough temperature, a median temperature, and/or other phases), an average temperature over a sliding window in time, and/or other measurements of temperature. The temperature of the radiation source may be determined as a function of the electrical resistance through the radiation source. In one embodiment, operation 64 is performed by a processor similar to or the same as processor 26 (shown in FIG. 1 and described herein).

At an operation 68, the provision of power to the radiation source at operation 55 is adjusted based on the temperature determined at operation 64. The adjustment may be intended to maintain the temperature of the radiation source within specific bounds. The bounds may include a range, a threshold, and/or other bounds. In one embodiment, operation 68 is performed by a processor similar to or the same as processor 26 (shown in FIG. 1 and described herein).

At an operation 70, an estimated irradiance of the radiation source is determined. Operation 70 may further include comparing the estimated irradiance with a measured irradiance. The estimated irradiance may be determined based on the output signals generated at operation 62. The measured irradiance may be determined based on the output signals generated at operation 60. The comparison performed at operation 70 may provide an indication of one or more phenomena which tend to degrade measurement accuracy. By way of non-limiting example, the comparison performed at operation 70 may indicate, if the difference between estimated and measured irradiance is relatively large, a change in measurement optical path, and/or other optical phenomena. In some embodiments, operation 70 is performed by a processor similar to or the same as processor 26 (shown in FIG. 1 and described above).

In some embodiments, responsive to a relatively large difference between estimated and measured irradiance at operation 70 (e.g., breaching a threshold difference), further actions may be performed at operation 72. Such further actions may include, for example, notifying a user, triggering a re-calibration, and/or other further actions to bring estimated and measured irradiance back into conformity. In some embodiments, operation 72 is performed by a processor similar to or the same as processor 26 (shown in FIG. 1 and described above).

At an operation 74, a level of a gaseous molecular species within the flow of breathable gas in the flow path is determined based on the output signals conveying information related to the parameter of the received electromagnetic radiation. The determination of the level of the gaseous molecular species is further based on the output signals generated at operation 74, in that the determination of the level of the gaseous molecular species accounts for the temperature of the radiation source (e.g., the electrical resistance through the source). This may include adjusting a determination of the level of a gaseous molecular species, and/or implementing an irradiance estimated at operation 70 as the reference irradiance (instead of a measured irradiance) in the determination of the level of a gaseous molecular species. In one embodiment, operation 74 is performed by a processor similar to or the same as processor 26 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method of monitoring a level of a gaseous molecular species within a flow of breathable gas with a detector, the method comprising:

estimating irradiance of a radiation beam before the beam passes through a flow path of a flow of breathable gas that communicates with an airway of a subject, the radiation beam including a first wavelength absorbed by a selected species in the breathable gas in the flow path and a second reference wavelength;

after the radiation beam has passed through the flow path, separating the first and second wavelengths into a first wavelength beam and a second wavelength beam, respectively;

with a first radiation detector, receiving the first wavelength beam and outputting an electronic signal indicative of the irradiance of the first beam;

comparing irradiance of the first wavelength beam with the estimated irradiance of the beam before passing through the flow path to determine a difference indicative of a level of the gaseous molecular species in the breathable gas in the flow path;

with a second radiation detector, receiving the second wavelength beam and outputting an electronic signal indicative of the irradiance of the second beam;

comparing the estimated irradiance of the beam before passing through the flow path with an irradiance of the second wavelength beam to determine a difference; and responsive to the difference between the estimated irradiance and the second wavelength beam irradiance exceeding a threshold, generating a notification to initiate a recalibration of the detector.

2. The method of claim 1, wherein estimating the irradiance of the radiation beam before passing through the flow path includes determining a resistance of a radiation source which generates the radiation beam and further including:

controlling a provision of power to the radiation source dynamically based on the determined electrical resistance.

3. The method of claim 1, wherein estimating the irradiance of the radiation beam before it passes through the flow path includes determining an electrical resistance of a radiation source that generates the radiation beam.

4. The method of claim 1, wherein separating the first and second wavelength beams includes:

passing the radiation beam, after passing through the flow path, through a beam splitter which separates the radiation beam into the first wavelength beam and the second wavelength beam.

5. The method of claim 4, further including:
generating an electronic output signal indicative of the irradiance of the first wavelength beam and generating a reference output signal indicative of the irradiance of the second wavelength beam; and
comparing the first and second output signals using a processor to determine a difference indicative of a level of a molecular species in the flow path.

6. The method of claim 3, further including:
converting the irradiance of the second wavelength beam into an electrical output signal indicative of the irradiance of the second wavelength beam;
with a processor, comparing the electrical resistance with the second output signal to determine the difference.

7. The method of claim 1, wherein the estimated irradiance is compared with the irradiance of the second wavelength beam using a processor.

8. The method of claim 1, wherein the molecular species is carbon dioxide wherein the irradiation beam before the beam passes through the flow path is in an infrared radiation band between 3 μm and 8 μm.

9. A detector configured to monitor a level of a gaseous molecular species within a flow of breathable gas, the detector comprising:
an flow path configured to pass a flow of the breathable gas that communicates with an airway of a patient;
at least one window in the flow path configured to pass a radiation beam such that the radiation beam passes across the flow path, the radiation beam including a first wavelength electromagnetic radiation which is absorbed by the gaseous molecular species and a reference wavelength electromagnetic radiation;
a beam splitter configured to separate the first wavelength electromagnetic radiation and the second wavelength electromagnetic radiation to generate a first beam and a second beam, respectively;
a first optical filter configured to pass the first wavelength electromagnetic radiation from the beam splitter;
a first radiation detector configured to receive the first wavelength electromagnetic radiation which has passed through the first optical filter and output an electronic signal indicative of the irradiance of the first beam;
a second optical filter configured to pass the second wavelength electromagnetic radiation from the beam splitter;
a second optical detector configured to convert the radiation of the second optical beam which has passed through the second filter into a second electrical signal indicative of irradiance of the second beam;
a computer processor configured to:
compare an estimated irradiance of the radiation beam before passing through the flow path with an irradiance of the electromagnetic radiation passing through the second optical filter to the second sensor to determine a difference,
compare the difference with a threshold and in response to the difference exceeding the threshold, generate a notification to a user of the detector to initiate a recalibration of the detector,
compare an irradiance of the first beam which passed through the first optical filter with an irradiance of the second radiation beam which passed through the second optical filter to determine a difference indicative of a level of the gaseous molecular species from the first and second electrical output signals.

10. The detector of claim 9, wherein the beam splitter is a dichroic mirror.

11. The detector of claim 10, further including at least one lens disposed adjacent the at least one window, the lens being configured to direct the radiation beam through the flow path to the dichroic mirror.

12. A non-transitory computer-readable medium configured to control a processor to perform the method of claim 1.

13. The detector of claim 9, further including at least one lens disposed adjacent the at least one window, the lens being configured to direct the radiation beam through the flow path to the beam splitter.

14. The detector of claim 9, wherein the molecular species is carbon dioxide wherein the irradiation beam before the beam passes through the flow path is in an infrared radiation band between 3 μm and 8 μm.

15. A carbon dioxide detector configured to monitor a level of carbon dioxide within a flow of breathing gas, the detector comprising:
a U-shaped housing including first and second legs, the first and second legs defining a gap therebetween, the gap being configured to receive a hollow airway assembly which carries breathing gas;
a radiation source disposed in the first leg, the radiation source being configured to emit light in a mid-wavelength infrared band and light of a reference wavelength;
a first lens disposed in the first leg adjacent the radiation source and configured to direct radiation from the radiation source across the gap to the second leg;
a beam splitter disposed in the second leg and configured to receive the light from the radiation source which has traversed the gap and to separate the mid-wavelength infrared light from light of the reference wavelength to generate a mid-wavelength infrared beam and a reference beam, respectively;
a first optical filter configured to pass the mid-wavelength infrared beam;
a first radiation detector configured to receive the mid-wavelength infrared beam which is passed through the mid-wavelength infrared filter and output an electronic signal indicative of irradiance of the mid-wavelength infrared beam;
a reference optical filter configured to pass the reference wavelength beam from the beam splitter;
a second optical detector configured to convert the referenced optical beam which has passed through the second filter into an electrical signal indicative of irradiance of the reference optical beam; and
a computer processor configured to:
compare an estimated irradiance of the radiation beam before passing across the gap with the irradiance of the reference optical beam passing through the reference optical filter to the second sensor to determine a difference,
compare the difference with a threshold and, in response to the difference exceeding a threshold, generate a notification to a user to initiate a recalibration of the detector, and
compare the irradiance of the mid-wavelength infrared beam which passed through the mid-wavelength infrared filter with the irradiance of the reference radiation beam which passed through the referenced optical filter to determine a level of the gaseous carbon dioxide in the sample gas airway.

\* \* \* \* \*